US012721661B2

(12) United States Patent
Hoffmann et al.

(10) Patent No.: US 12,721,661 B2
(45) Date of Patent: Sep. 1, 2026

(54) IMPLANTABLE DEVICE, IN PARTICULAR OF THE INTER VERTEBRAL SPACER TYPE

(71) Applicant: COUSIN BIOTECH, Wervicq Sud (FR)

(72) Inventors: Eléonore Hoffmann, Wambrechies (FR); Lucie Becquart, Lille (FR); Michel Caillibotte, Lille (FR)

( * ) Notice: Subject to any disclaimer, the term of this patent is extended or adjusted under 35 U.S.C. 154(b) by 589 days.

(21) Appl. No.: 17/924,131

(22) PCT Filed: May 11, 2021

(86) PCT No.: PCT/EP2021/062514
§ 371 (c)(1),
(2) Date: Nov. 9, 2022

(87) PCT Pub. No.: WO2021/228876
PCT Pub. Date: Nov. 18, 2021

(65) Prior Publication Data

US 2023/0172643 A1 Jun. 8, 2023

(30) Foreign Application Priority Data

May 14, 2020 (FR) ....................................... 2004780
Feb. 2, 2021 (FR) ....................................... 2100980

(51) Int. Cl.
*A61B 17/70* (2006.01)

(52) U.S. Cl.
CPC ...... *A61B 17/7061* (2013.01); *A61B 17/7065* (2013.01); *A61B 17/7067* (2013.01)

(58) Field of Classification Search
CPC ............ A61B 17/7053; A61B 17/7061; A61B 17/7062; A61B 17/7064; A61B 17/7065; A61B 17/7067; A61F 2/4405
See application file for complete search history.

(56) References Cited

U.S. PATENT DOCUMENTS

2006/0084988 A1* 4/2006 Kim .................. A61B 17/7065 606/279
2006/0282075 A1 12/2006 Labrom et al.
2007/0106298 A1* 5/2007 Carli ................. A61B 17/7065 623/17.13
2008/0114456 A1* 5/2008 Dewey .............. A61B 17/7065 623/17.16
2008/0183209 A1 7/2008 Robinson et al.
2009/0216274 A1* 8/2009 Morancy-Meister ........................ A61B 17/7065 606/247
2010/0121456 A1 5/2010 Taylor
(Continued)

FOREIGN PATENT DOCUMENTS

FR 2844179 A1 3/2004

*Primary Examiner* — Nicholas J Plionis

(57) ABSTRACT

An implantable device including an intervertebral wedge including an upper bearing zone and a lower bearing zone and at least one first lateral spring having a position A relative to the intervertebral wedge in a position for inserting the implantable device and a position B relative to the intervertebral wedge in a position for implanting the implantable device, the positions A and B being different and the first lateral spring being configured: to freely translate from position A to position B and to form a retention component arranged relative to the intervertebral wedge to block the migration of the intervertebral wedge toward the spinal canal in position B.

19 Claims, 13 Drawing Sheets

(56) References Cited

U.S. PATENT DOCUMENTS

| | | | | |
|---|---|---|---|---|
| 2010/0131009 | A1 | 5/2010 | Roebling et al. | |
| 2010/0234951 | A1* | 9/2010 | Koske | A61B 17/7071 606/248 |
| 2011/0029021 | A1* | 2/2011 | Hartsell | A61B 17/7065 606/249 |
| 2011/0046674 | A1* | 2/2011 | Calvosa | A61B 17/7065 606/249 |
| 2011/0166600 | A1* | 7/2011 | Lamborne | A61B 17/7064 606/249 |
| 2012/0215262 | A1* | 8/2012 | Culbert | A61B 17/8625 606/279 |
| 2013/0023990 | A1 | 1/2013 | Zipnick et al. | |
| 2018/0146989 | A1 | 5/2018 | Hwang et al. | |

* cited by examiner

[Fig. 1]
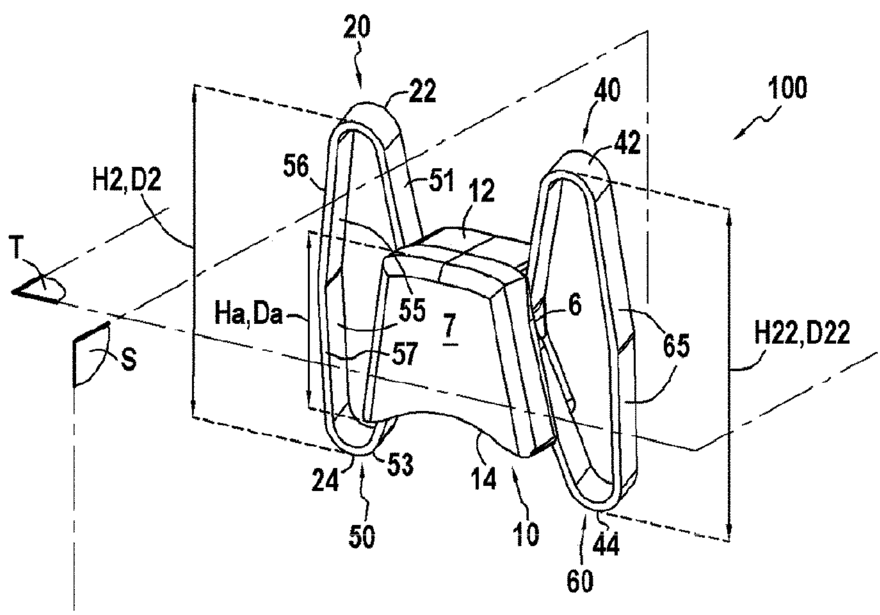
[Fig. 2]
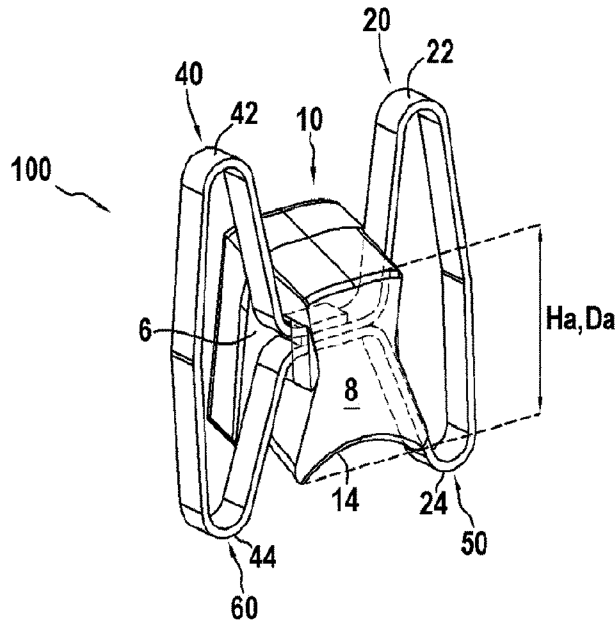

[Fig. 3]
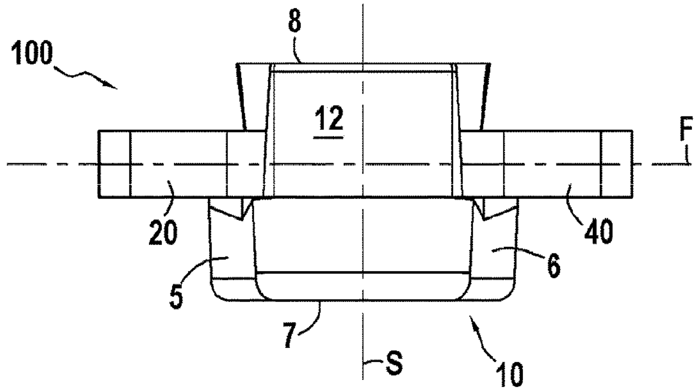
[Fig. 4]
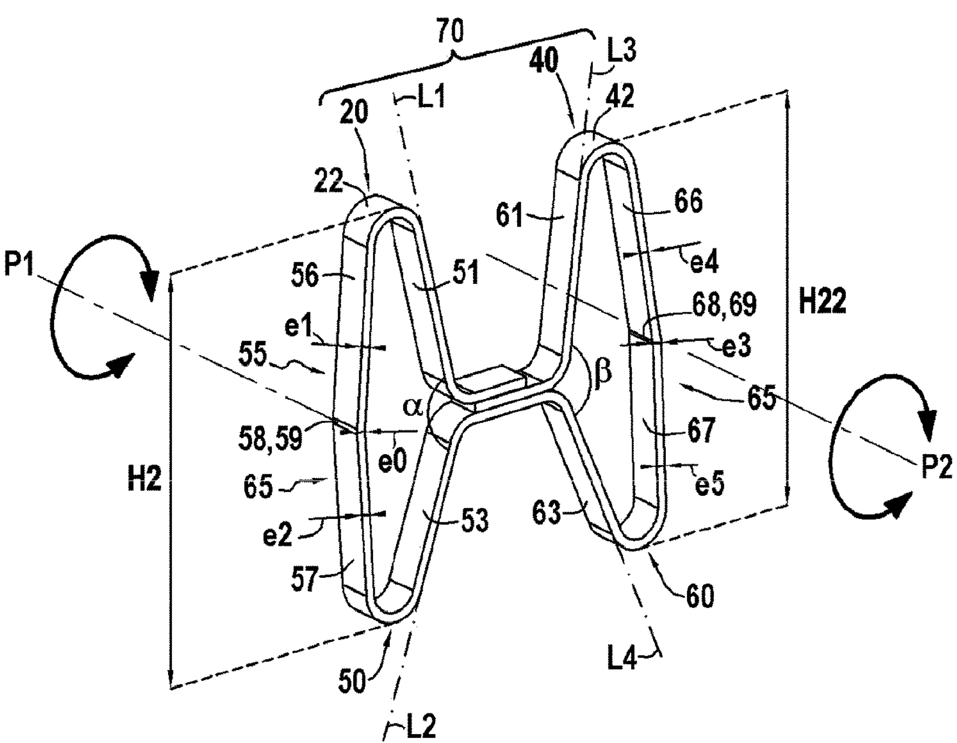

[Fig. 5]
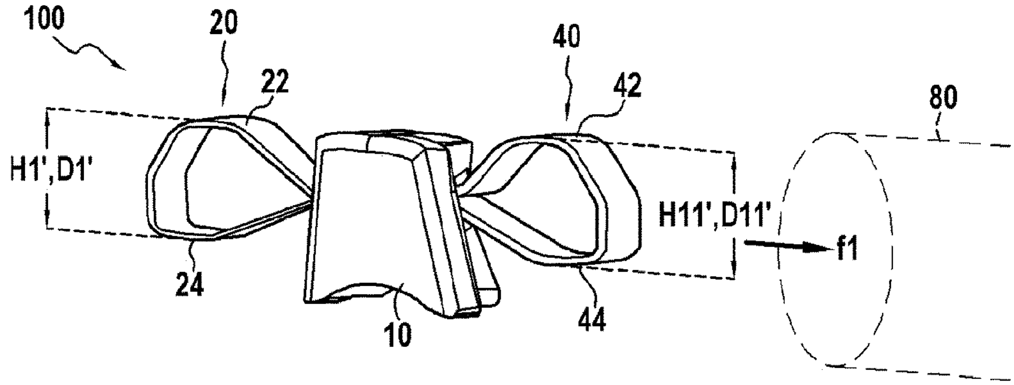
[Fig. 6]
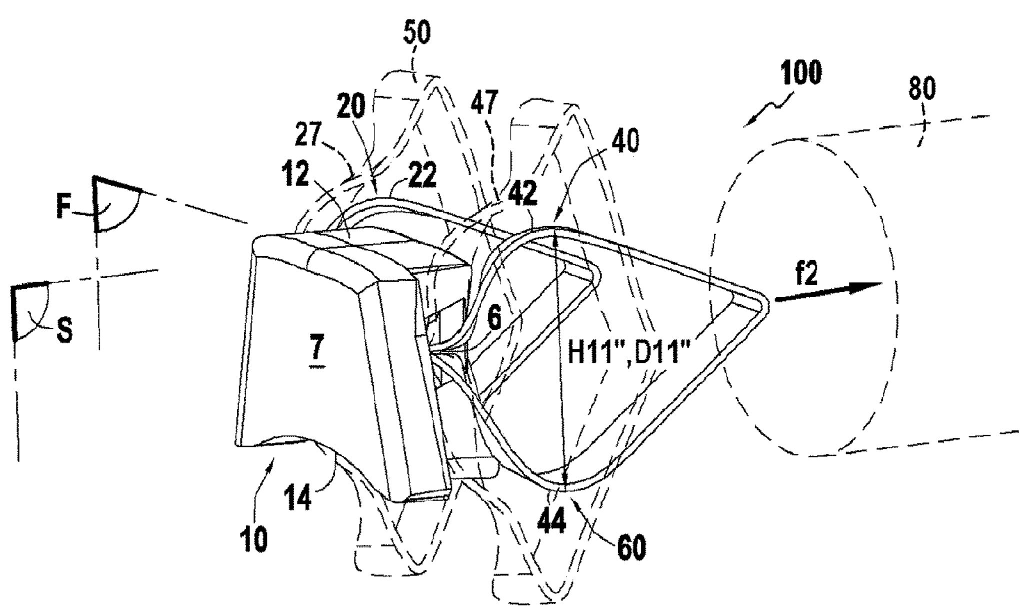

[Fig. 7]
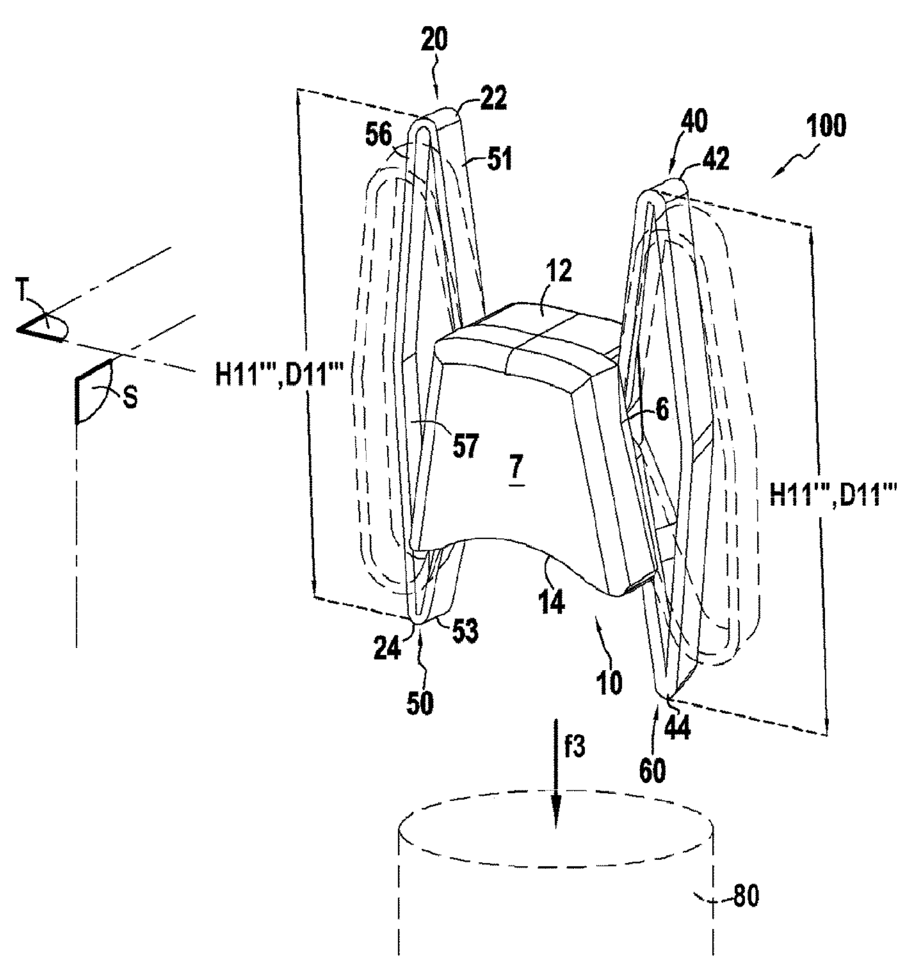

[Fig. 8]
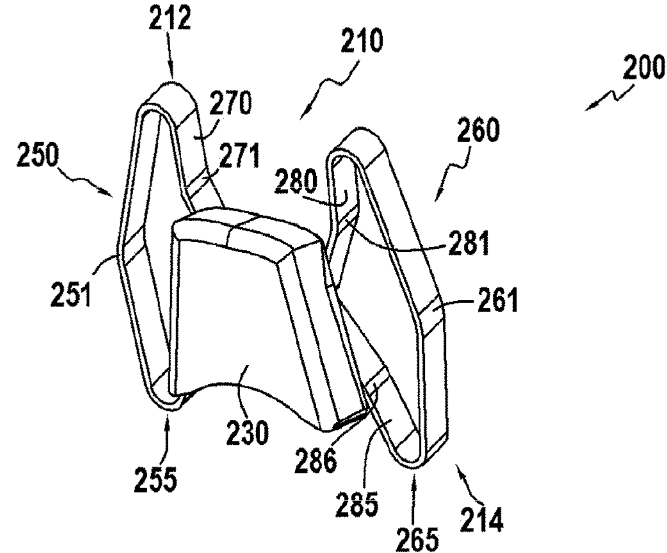
[Fig. 9]
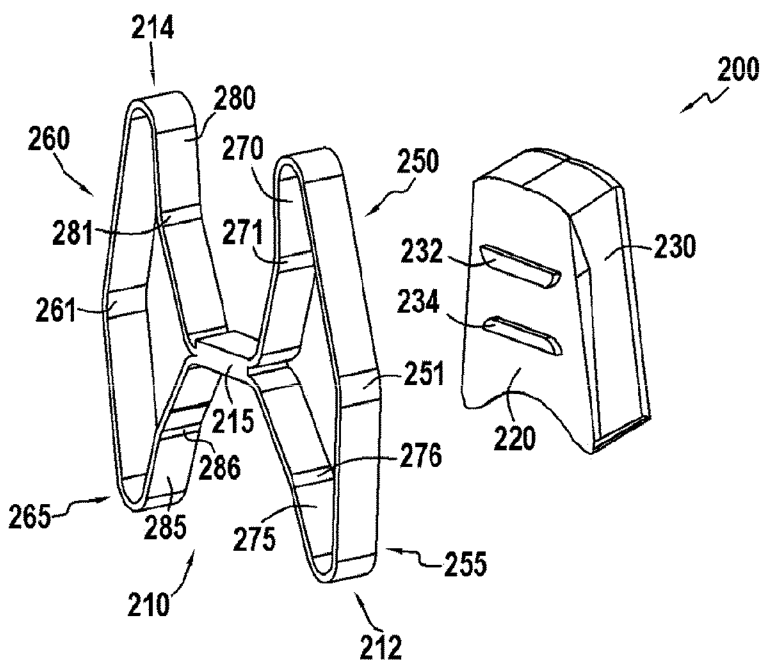

[Fig. 10]
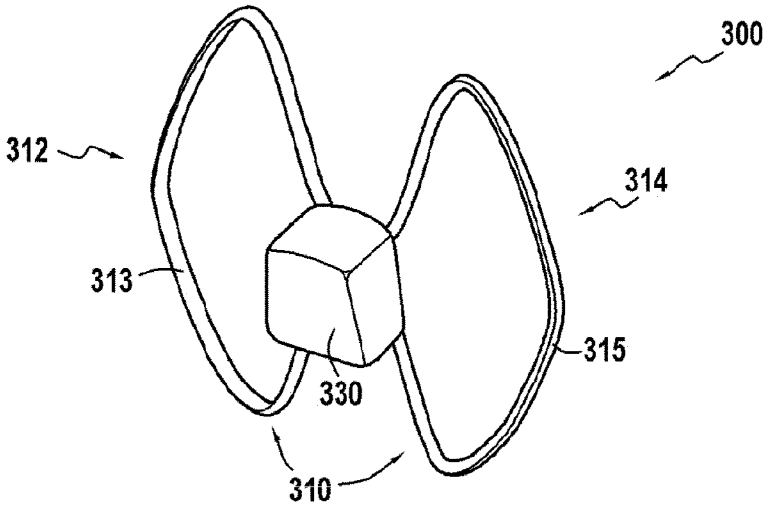
[Fig. 11]
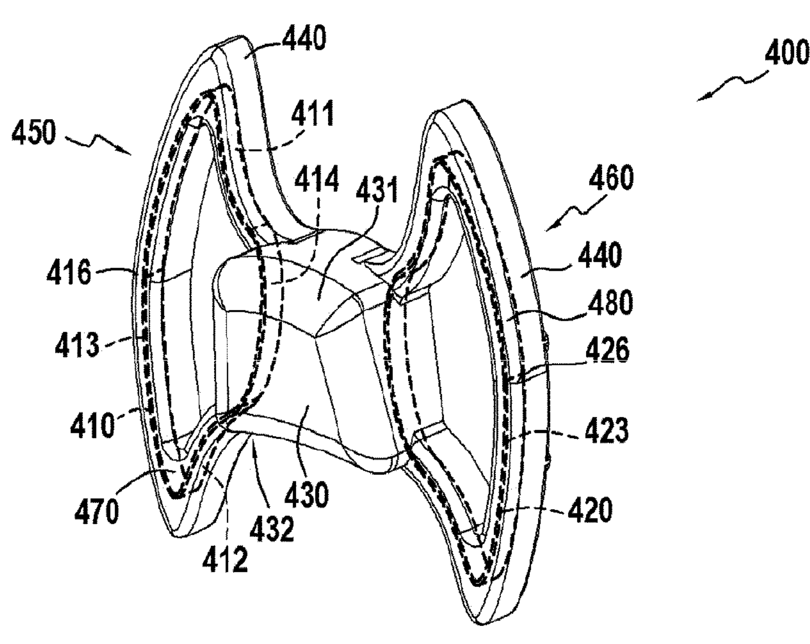

[Fig. 12]
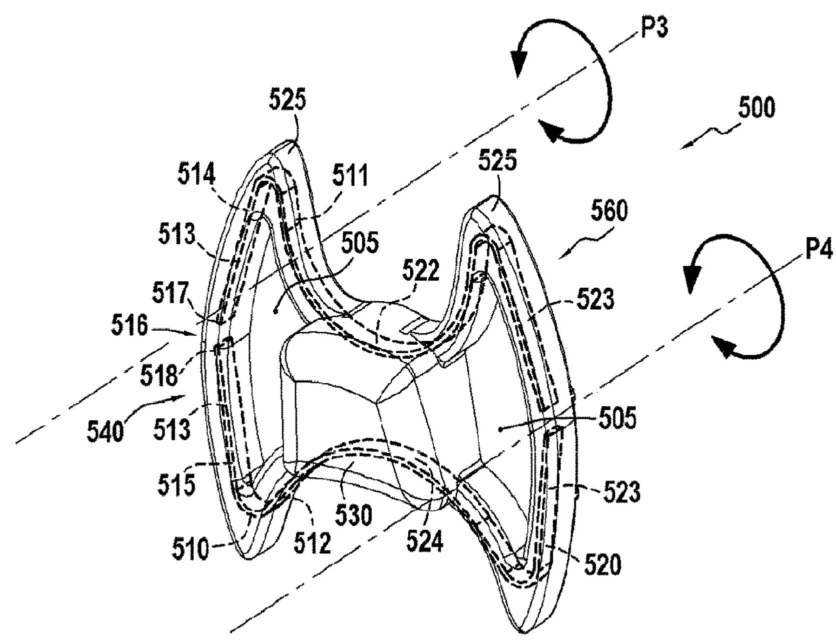
[Fig. 13]
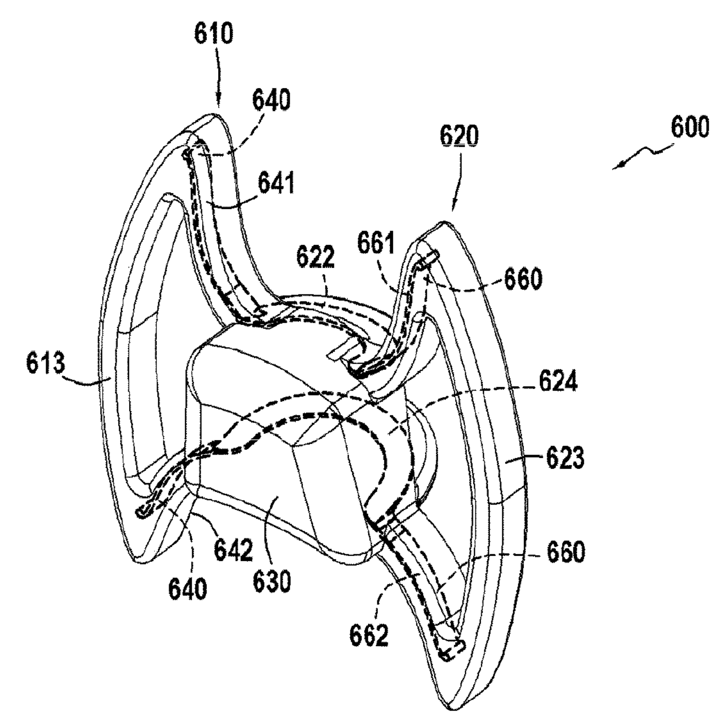

[Fig. 14]
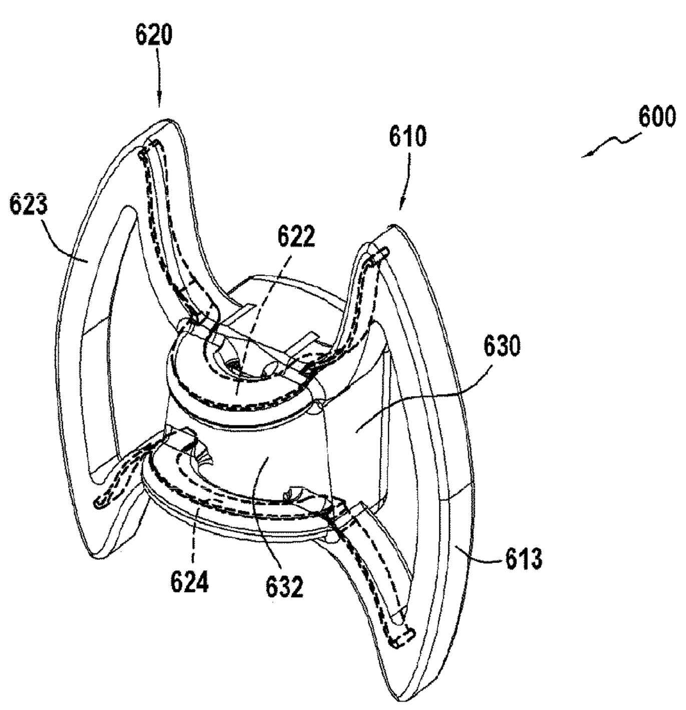

[Fig. 15]
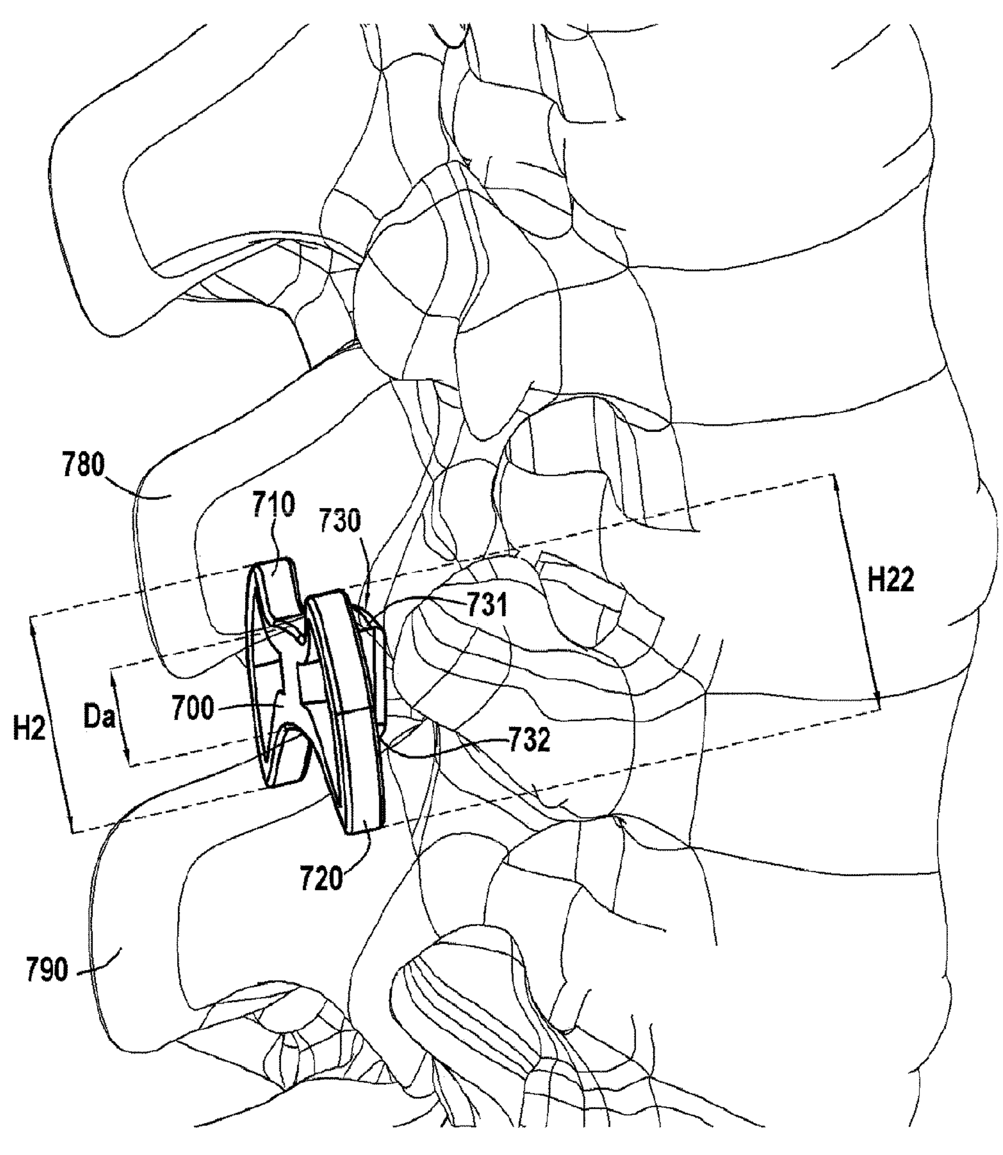

[Fig. 16]
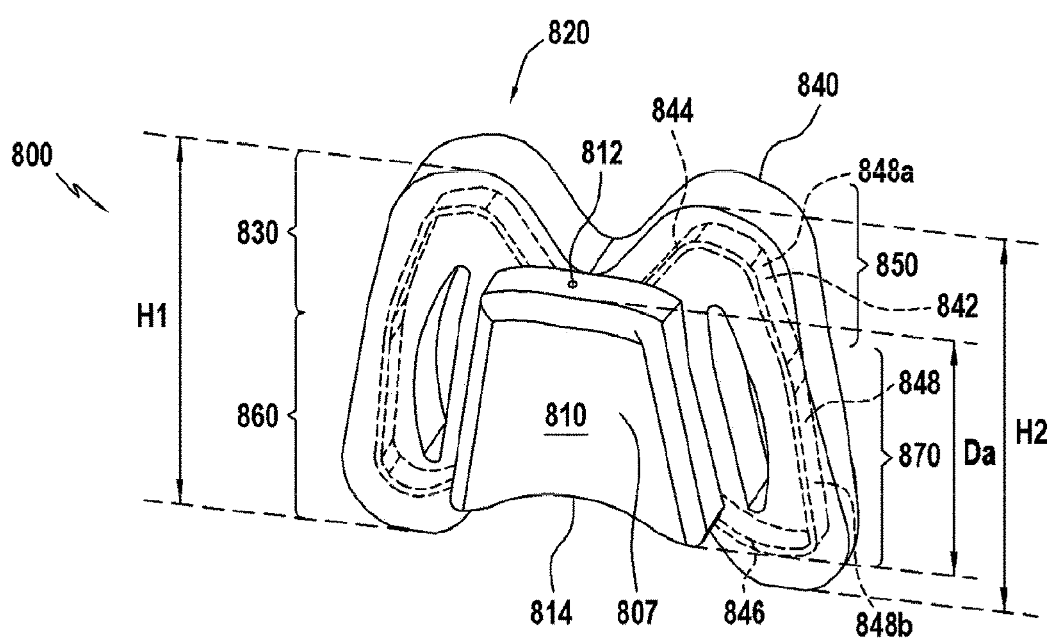

[Fig. 17]
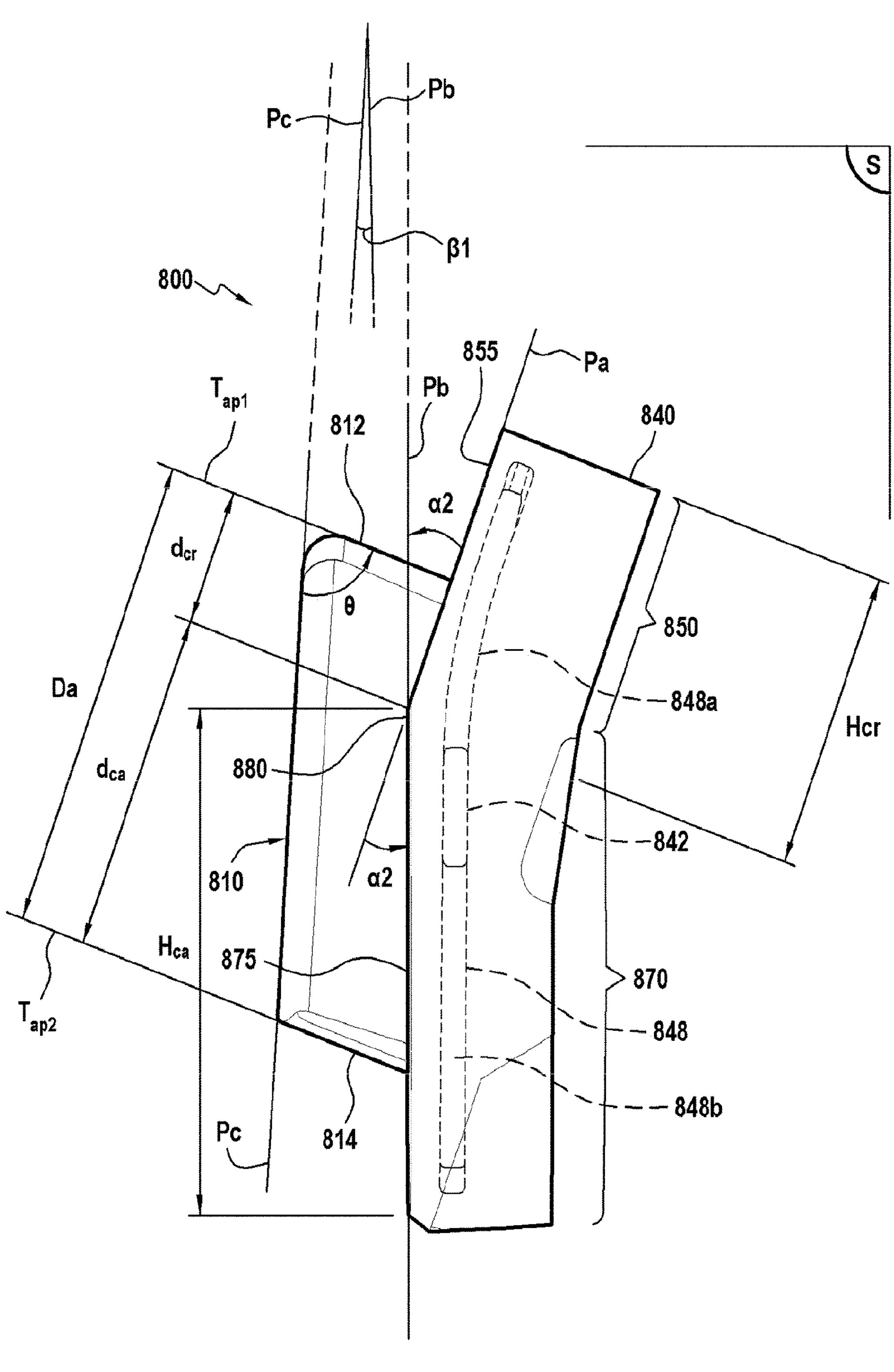

[Fig. 18]
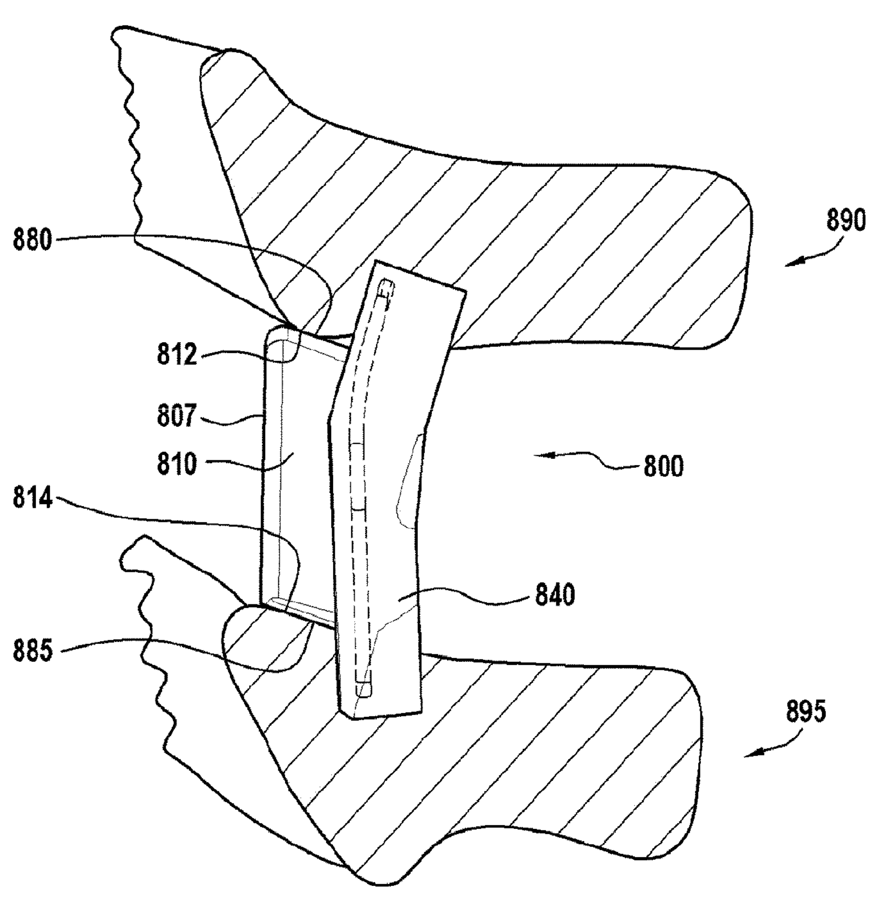

[Fig. 19]
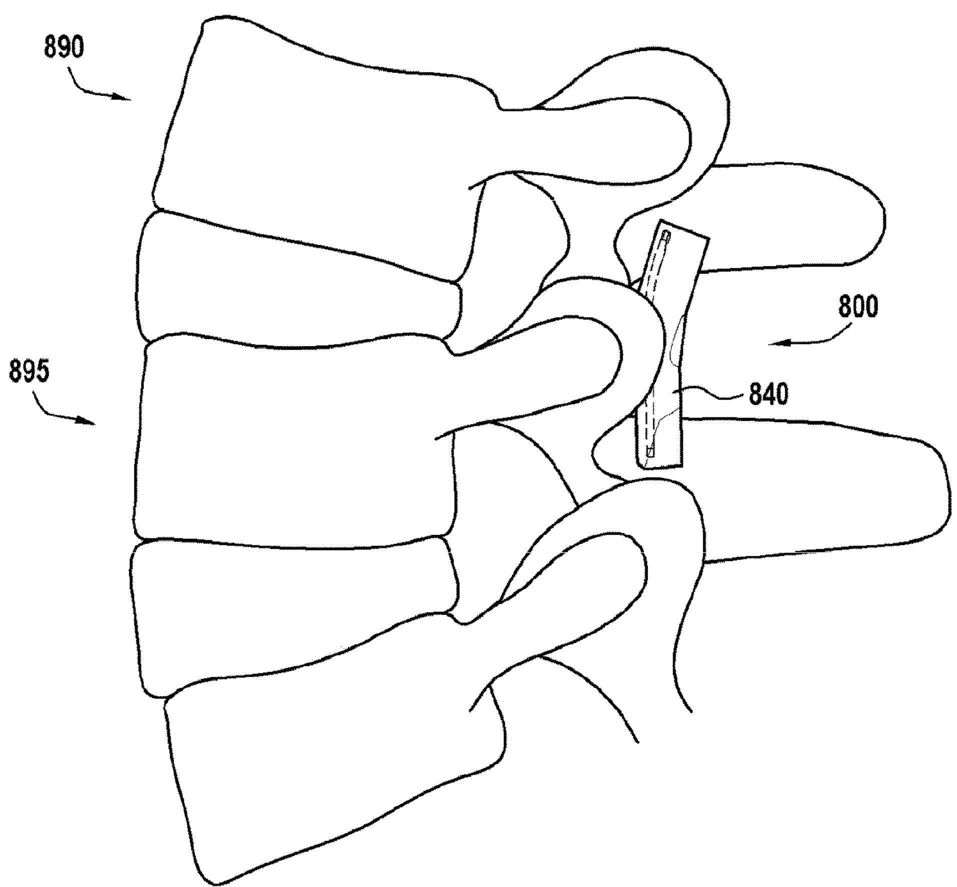

IMPLANTABLE DEVICE, IN PARTICULAR OF THE INTER VERTEBRAL SPACER TYPE

TECHNICAL FIELD

The subject matter of the present disclosure is an implantable device, particularly of the intervertebral spacer type, for the treatment of at least one level of the spine.

BACKGROUND

These implantable devices, in particular of the intervertebral spacer type, function to redistribute loads and excess loads between two adjacent vertebrae (designated in the present text by underlying and overlying vertebrae), for example created by disc degeneration (especially in the case of a herniated disc).

The vertebrae of the human spinal column are positioned in a column with one vertebra on top of the next. The intervertebral disc is found between the underlying and overlying vertebrae to transmit forces between the vertebrae and to dampen these forces.

The discs also make it possible for the spinal column to bend (during flexion and extension movements of the subject) and twist (during flexion and extension movements of the subject). Over time, the intervertebral discs degrade, in other words, degenerate. This degeneration leads to a loss of fluids in the discs and makes them less flexible. Likewise, the discs become thinner which allows the vertebrae to move closer together. Degeneration can also lead to tears or cracks in the outer layer, or annulus, of the disc. The disc may start to swell to the outside of the disc.

Under all these conditions, the spaces through which the spinal cord and spinal nerve roots pass can become narrow, leading to pressure on the nervous tissue that can cause pain, numbness, weakness or even paralysis in various parts of the body. Finally, the facet joints between adjacent vertebrae may degenerate and cause localised and/or radiating pain.

All the symptoms and problems above are considered individually or in combination as a spinal cord disorder.

In order to treat them, surgeons try to re-establish the normal space between adjacent vertebrae. This may be sufficient to relieve the pressure on the affected nervous tissue. However, it is often necessary to surgically remove disc material, bone or other tissues that impinge on the nervous tissue and/or debride the facet joints. Most often, the intervertebral space is restored by inserting a solid spacer made of bone, metal or plastic into the disc space between adjacent vertebrae.

The techniques for positioning intervertebral spacers are invasive, generally by open surgery, because they require placing the prosthetic material deep in the surgical site adjacent to the vertebral column. Recovery from such a procedure may require several days in the hospital and a slow and prolonged readjustment to normal activity levels.

There is therefore a need for intervertebral spacers that can be inserted via surgical techniques that are as minimally invasive as possible. One example of such a surgical technique is the one developed by the Tsunami company involving lateral cutaneous implantation, but without a trocar. For example, this includes of making at least one incision, then passing a guide wire through this incision to guide the placement of the implantable device at the level of the spinal column to be treated through the tissues. The fluoroscopy technique can be used at the same time in order to assist the surgeon in the placement of implantable devices. However, in this technique, the implantable device is forced through the tissues along the guide wire and can therefore damage them. Another spinal procedure technique is a so-called minimally-invasive spine surgery (MISS) technique involving at least two trocars or conduits (tubes). A first conduit receives a camera and a second conduit allows the passage of the implantable device and surgical tool(s). The advantage of this technique is that the passage to the area of the spine to be treated is framed by one of the conduits so that the implantable device does not damage tissue when it is positioned on the site of the spine to be treated.

This MISS technique has not yet been used for intervertebral spacers, since these spacers are large and made of rigid material in order to maintain a minimum intervertebral space once implanted.

Some interspinous vertebral spacers are arranged to be implanted percutaneously using guide wire. Such a spacer, for example the one sold under the name Superion by the Vertiflex company, includes parts pivotally mounted on a support to have a compact configuration in the insertion position and a deployed position in the implantation position. The rigid parts are pivoted by the surgeon from the insertion position to the implantation position and held in this second position using a clamping mechanism. Stability on the level of the spine receiving the implant is also obtained by clamping the pivoting parts onto the spinous processes.

There is therefore a risk of these pivoting parts breaking under the effect of loads and excess loads. Furthermore, this implantable device cannot be implemented using one of the MISS techniques including of placing a single trocar laterally relative to the sagittal plane passing through the supraspinous ligament. Indeed, when wishing to position an implantable device posteriorly, it is recommended that the trocar not be in the same plane relative to the one passing through the supraspinous ligament in order not to damage it. This implies that the device must come out of the trocar to be positioned in the interlaminar or interspinous operating site by negotiating a bend. However, the SUPERION device intended to be implanted in an interspinous position cannot be positioned by this technique because it is too cumbersome and rigid to easily pass through this bend. As a result, this SUPERION device is placed in a trocar that crosses through the supraspinous ligament and therefore irreversibly damages the supraspinous ligament.

SUMMARY

The subject matter of the present disclosure is an implantable device, in particular for maintaining an intervertebral space between overlying and underlying vertebrae which can be implanted by a less invasive technique, percutaneously or by minimally-invasive route (MISS) via trocars.

The subject matter of the present disclosure is an implantable device making it possible to maintain an intervertebral, in particular interlaminar, space at the level of the vertebral column treated, while providing dynamic stability, that is to say allowing a certain mobility between the overlying and underlying vertebrae treated. The implantable device according to the disclosure can be used, in a non-limiting manner, to treat pathologies such as herniated disc, spinal canal stenosis, and/or disc degeneration.

The subject matter of the present disclosure according to a first aspect is an implantable device, especially for maintaining an intervertebral space between an overlying and underlying vertebrae, including:

an intervertebral wedge including an upper bearing zone, in particular over at least a portion of the lamina of the overlying vertebra, and a lower bearing zone, in particular over at least a portion of the lamina of the underlying vertebra, separated by a minimum distance Da to maintain an intervertebral space, and at least one first lateral spring having a position A relative to the intervertebral wedge in a position for inserting the implantable device and a position B relative to the intervertebral wedge in a position for implanting the implantable device, the positions A and B being different. The first lateral spring is configured:

to freely translate from position A to position B, and to form a retention component arranged relative to the intervertebral wedge to block the migration of the intervertebral wedge toward the spinal canal in position B.

Advantageously, the implantable device includes a part of its structure formed by a first lateral spring and, optionally, a second lateral spring (similar to the first lateral spring) making it possible to reduce the size of the implantable device by reversible deformation thereof to place it in an insertion position. Due to the specific inherent structure of a spring, in particular its elastic properties, the first lateral spring recovers its implantation position automatically, quickly or slowly, once released onto the implantation site, without irreversible deformation and/or clamping being done using at least one clamping means and an ancillary for manipulating the implantable device allowing it to translate from the insertion position to the implantation position.

Preferably, the first lateral spring includes a first region that brings the intervertebral wedge closer or further away when it is placed in position A, corresponding to the insertion position of the implantable device.

Preferably, the second lateral spring includes a second region that brings the intervertebral wedge closer or further away when it is placed in position A, corresponding to the insertion position of the implantable device.

Insertion position is understood to mean the position in which the implantable device has a reduced footprint in at least one direction relative to its implantation position and/or the position in which the implantable device is constrained to deform, especially elastically, thus facilitating its insertion in a conduit of given inner diameter, especially a trocar. The tube can have an inner diameter greater than or equal to 5 mm and less than or equal to 50 mm, for example around 12 mm.

Insertion position means the position adopted by the implantable device at the level of the spine treated and/or the position of the implantable device free of any constraint aimed at deforming it to hold it in the insertion position, in particular at a temperature greater than or equal to As (start austenite temperature) with, for example, an As of around 15° C., especially for a titanium nickel alloy.

In one embodiment, the first lateral spring (and/or the second lateral spring) are in a frontal plane F1 (or in respective frontal planes F1 and F2), especially essentially parallel to frontal plan F of the intervertebral wedge in position A and position B. For example, the first lateral spring and/or the second lateral spring each have a height that is increased or decreased in the frontal plane F1 and/or in the frontal plane F2.

Preferably, the planes F1 and F2 are essentially parallel, in particular coincident.

In another embodiment, the first lateral spring is in a sagittal plane S1 and/or the second lateral spring is in a sagittal plane S2, especially essentially parallel to the sagittal plane S of the intervertebral wedge, in position A; and the first lateral spring is in a frontal plane F1 and/or the second lateral spring is in a frontal plane F2, in position B, especially essentially parallel to the frontal plane F of the intervertebral wedge, planes S1 and/or S2 being intersecting with the plane(s) F1 and/or F2, in particular essentially perpendicular. For example, the first lateral spring and/or the second lateral spring are folded down against the intervertebral wedge in position A.

The first lateral spring and, optionally, the second lateral spring described below are placed in position A, corresponding to the insertion position of the implantable device, by applying a consistent mechanical constraint to compress the first (or second) lateral spring, for example using an ancillary and/or by positioning the implantable device in a tube; this constraint makes it possible to bring together or move apart two distinct regions of the first lateral spring and/or of the second lateral spring and therefore to deform it or them elastically.

Preferably, the first lateral spring and/or the second lateral spring have positions A in which they are deformed. However, a deformation position A is preferred for the operation of the first and/or second lateral springs depending on the construction of the implantable device.

Preferably, the first lateral spring and/or the second lateral spring include at least one material including at least one implantable and elastic metal or metal alloy, for example a stainless steel material and/or a material with shape memory.

At least one elastic metal is understood to mean any metal able to undergo reversible deformations, in particular at a temperature included between 0° C. and 40° C.

The first lateral spring and, optionally, the second lateral spring, are placed in position B, corresponding to the implantation position of the implantable device, by removing the mechanical deformation constraint applied in position A, and/or by thermal input activating the return to a so-called trained shape corresponding to position B of the first and/or second lateral spring(s).

Preferably, the first lateral spring (and, optionally, the second lateral spring) are positioned in position B freely, under the effect of their intrinsic elasticity and/or under the effect of thermal activation, in particular with no external assistance to the device, for example of the clamping device type holding the implantable device in its implantation position.

In particular, the first lateral spring (and optionally the second lateral spring) are positioned in position B due to their intrinsic properties: i.e., construction, especially including one or more mechanical spring zones and/or materials that comprise, for example at least one shape-memory material and/or at least one elastic metal.

The insertion of the implantable device according to the disclosure into the site of the spine to be treated advantageously makes it possible not to damage the supraspinous ligament. Indeed, the implantable device can be inserted and routed into its insertion position in a trocar, positioned at a distance, to the right or left of the supraspinous ligament and, optionally, including a bend at its distal end.

"Freely" is understood to mean that no external mechanical constraint, especially permanent (by means of a clamping and/or locking device or ancillary) is applied to the first lateral spring (and/or to the second lateral spring) to allow it to be placed in position B from its position A.

In a preferred embodiment, the implantable device includes a second lateral spring having position A relative to the intervertebral wedge in a position for inserting the implantable device and position B relative to the intervertebral wedge in a position for implanting the implantable device, the positions A and B being different. The second lateral spring is configured:

to freely translate from position A to position B and to form a retention component arranged relative to the intervertebral wedge to block the migration of the intervertebral wedge toward the spinal canal in position B.

Preferably, everything which is described in the present text (variants and subvariants of embodiment, definitions, modes of embodiment, etc.) in reference to the first lateral spring integrally applies to the second lateral spring.

In one embodiment, the first lateral spring and/or the second lateral spring are reversibly deformable, especially elastically, in particular at a temperature greater than or equal to 0° C. and less than or equal to 37° C.

Reversibly deformable is understood to mean that the first lateral spring and/or the second lateral spring can be deformed to translate from position A to implantation position B and vice versa.

The term sagittal section plane in the present text is understood to mean the sagittal section plane S of the intervertebral wedge according to the disclosure, in particular corresponding essentially to the sagittal section plane of the human body passing essentially through the sagittal section plane S of the intervertebral wedge of the implantable device in its implantation position.

The term frontal section plane F in the present text is understood to mean the frontal section plane F of the intervertebral wedge according to the disclosure, in particular corresponding essentially to the frontal section plane of the human body passing essentially through the frontal section plane F of the intervertebral wedge of the implantable device in its implantation position.

The term transverse section plane T in the present text is understood to mean the transverse section plane T of the intervertebral wedge according to the disclosure, in particular corresponding essentially to the transverse section plane of the human body passing essentially through the transverse section plane T of the intervertebral wedge of the implantable device in its implantation position.

The intervertebral wedge according to the disclosure is configured to maintain an intervertebral space between the overlying and underlying vertebrae, in particular so as to dynamically stabilise the level of the spine provided with the implant.

The intervertebral wedge is preferably dimensioned to fill the implantation area, i.e., the interlaminar area treated to be close to the centre of rotation of the overlying and underlying vertebrae and be positioned in the most solid area of the vertebrae, i.e., the lamina.

Preferably, the intervertebral wedge is configured to be able to be lightly compressed, especially in a direction extending from the upper bearing zone to the lower bearing zone, in use, to conserve the movements of the vertebral segment treated.

The expressions configured for, suitable for and suited to are equivalent in the present text.

In the embodiments, the intervertebral wedge includes the first and second lateral zones, especially positioned on either side of a sagittal section plane S of the intervertebral wedge. The intervertebral wedge preferably includes the front and rear zones, especially positioned on either side of a frontal section plane F of the intervertebral wedge.

Preferably, the first and second lateral springs are positioned on either side of the sagittal section plane (S) of the intervertebral wedge.

Preferably, the first and second lateral springs respectively extend from the first and second lateral zones of the intervertebral wedge.

In one embodiment, the intervertebral wedge includes at least one polymer material, in particular elastomer, especially (over) moulded, and/or at least one textile.

The polymer material can be chosen from among silicones and polyurethanes or a combination of these.

The textile can be a knit, a weave, a nonwoven fabric, a braid, a cable or a combination of these.

Preferably, the textile includes one or more monofilament yarn(s) and/or one or more multifilament yarn(s) and/or one or more yarns spun from fibres.

The yarn(s) defined in the present text can include (be made up of) one or more partially or completely resorbable or nonresorbable biocompatible polymer materials.

The material(s) can be chosen from: polyolefins, such as polypropylene, polyethylene; polyesters, such as ethylene or butylene polyethylene terephthalate; polyurethanes and resorbable polymers, especially including polylactic acid (PLLA, PLDA, etc.).

In a variant, the at least first lateral spring has a height H1 in position A and a height H2 in position B, H2 being different from H1.

In a first embodiment, H1 is less than H2.

In a second embodiment, H1 is greater than H2.

Preferably, the implantable device includes a second lateral spring having a height H11 in position A and a height H22 in position B, H22 being different from H11.

In a first embodiment, H11 is less than H22.

In a second embodiment, H11 is more than H22.

The first embodiment and the second embodiment correspond to two different positions A of the first and/or second lateral springs.

In a variant of embodiment, the first lateral spring includes at least one material chosen from shape-memory materials.

Shape-memory materials are preferably metal shape-memory materials.

The at least one shape-memory material can be chosen from: an alloy including at least titanium and, optionally, nickel; in particular, the titanium and nickel are in essentially equal mass proportions. The alloy can be Nitinol.

Preferably, the second lateral spring includes at least one material chosen from shape-memory materials, especially metal.

The first lateral spring and/or the second lateral spring have been shaped (in particular by applying a heat treatment during their manufacture) according to a determined shape, in particular to shape B according to the disclosure, so that the first lateral spring and/or the second lateral spring regain the shape B by heat activation of the remembered shape B.

The shape-memory material is preferably determined, in particular its composition, according to the start austenite (As) and finish austenite (Af) temperatures considered. The As temperature defines the temperature from which the shape-memory material starts to move toward its trained shape and Af the temperature at which the shape memory material returns to its trained shape.

For example, As can be around 15° C. for the shape-memory material selected for the first and/or the second lateral springs. Thus, at a temperature below approximately 15° C., the shape-memory material is in a plastic state and at a temperature greater than approximately 15° C., the material is in a superelastic state. As can be around 35° C.-35° C., for example, so that the shape-memory material is in a plastic state at room temperature and superelastic at body temperature once implanted.

It is also possible to store the implantable device in its implantation position, for example positioned in a hollow tube, at room temperature or in a cooling device so that the springs are in a plastic state and therefore easily deformable.

The skilled person who knows shape-memory materials knows to adapt the composition of the metal alloy to adjust the As and Af temperatures according to the desired implantation conditions.

In a variant of embodiment, the first lateral spring includes first upper and lower portions separated by D1 in position A and separated by D2 in position B, D2 being different from D1 and the implantable device is positioned in the insertion position by bringing together or separating the first upper and lower portions of the first lateral spring.

When the first upper and lower portions are moved closer to each other, D2 is greater than D1 and when they are separated, D2 is less than D1.

In some embodiments, the second lateral spring includes second upper and lower portions separated by D11 in position A and separated by D22 in position B, D22 being different from D11, for example greater or lesser than D11 and the implantable device is positioned in the insertion position by bringing together or separating the first upper and lower portions of the second lateral spring.

In some embodiments, the distance D1 essentially corresponds to the height H1 and the distance D2 essentially corresponds to the height H2 and/or the distance D11 essentially corresponds to the height H11 and the distance D22 essentially corresponds to the height H22.

Preferably, the first upper and lower portions of the first lateral spring project on either side of a transverse section plane T of the intervertebral wedge.

Preferably, the second upper and lower portions of the second lateral spring project on either side of a transverse section plane T of the intervertebral wedge.

In a variant of embodiment, the intervertebral wedge has a maximum height Ha and Ha is less than H2 and/or H22 in the insertion position.

Advantageously the first lateral spring and, optionally, the second lateral spring project above the upper bearing zone of the intervertebral wedge and/or below the lower bearing zone of the intervertebral wedge.

This arrangement advantageously allows the first lateral spring and, optionally, the second lateral spring to block the migration of the intervertebral wedge toward the spinal canal.

In a variant of embodiment, the first lateral spring extends from one side of a sagittal section plane (S) of the intervertebral wedge.

In some of embodiments, the second lateral spring extends from one side of a sagittal section plane (S) of the intervertebral wedge, especially in the second lateral area of the intervertebral wedge.

In a variant of embodiment, the first lateral spring includes a first armature including one or more at least partially metallic elongated elements, such as a ribbon or a wire.

In some embodiments, the second lateral spring includes a second armature including one or more at least partially metallic elongated elements, such as a ribbon or a wire.

The section of the elongated metal element(s) can be essentially circular or oval or parallelepipedal, especially rectangular.

The elongated elements can include one or more metal shape-memory materials and/or one or more metal materials based on elastic stainless steel.

Preferably, the first armature and/or the second armature are made up of at least partially metallic elongated elements according to the disclosure.

In some embodiments, the first armature and/or second armature each include one or more bending zones, especially arranged in the at least partially metallic elements according to the disclosure. In particular, the thickness of a bending zone is less than the mean thickness of the elongated element including the bending zone.

The bending zones preferably form one or more leaf springs.

In some embodiments, the first armature and the second armature include at least one partially metallic elongated element, in common, or each include one or more distinct at least partially metallic elongated elements.

In one embodiment, the intervertebral wedge is overmoulded on: at least a part of the first armature and/or on at least a part of the second armature and/or on at least a part of the main armature (defined below). This arrangement allows reliably joining the intervertebral wedge to the first and/or second armatures and/or to the main armature.

In a variant of embodiment, the first armature includes a first upper arm and a first lower arm which diverge from each other.

In some embodiments, the second armature includes a second upper arm and a second lower arm which diverge from each other.

Preferably, the first upper arm and/or the first lower arm and/or the second upper arm and/or the second lower arm each include at least one portion in connection with the intervertebral wedge.

In some embodiments, the first upper arm passes essentially through an axis L1 and the first lower arm passes essentially through an axis L2, L1 and L2 being intersecting and forming an angle $\alpha$ greater than or equal to 45°, in particular greater than or equal to equal to 90°.

In some embodiments, the second upper arm passes essentially through an axis L3 and the second lower arm passes essentially through an axis L4, L3 and L4 being intersecting and forming an angle $\beta$ greater than or equal to 45°, in particular greater than or equal to equal to 90°.

In some embodiments, the first upper and lower arms and/or the second upper and lower arms (each) include a free end.

In a variant of embodiment, the first armature includes a first intermediate arm, continuous or discontinuous, in connection with the first upper arm and with the first lower arm.

In some embodiments, the second armature includes a second intermediate arm, continuous or discontinuous, in connection with the second upper arm and with the second lower arm.

Discontinuous is understood to mean that the first intermediate arm and/or the second intermediate arm is interrupted.

In a subvariant of embodiment, the first intermediate arm includes first upper and lower intermediate portions converging towards a first intermediate zone around which the first upper and lower intermediate portions pivot when moving from position A to position B.

In some embodiments, the second intermediate arm includes second upper and lower intermediate portions converging towards a second intermediate zone around which the second upper and lower intermediate portions pivot when moving from position A to position B.

The first (or second) upper and lower intermediate portions can also pivot around the first (or second) intermediate zone to translate from position B to position A.

In some embodiments, the first upper intermediate portion passes essentially through an axis A1 and the first lower intermediate portion passes essentially through an axis A2, A1 and A2 being intersecting and forming an angle greater than or equal to 45°, in particular greater or equal to 90°.

In some embodiments, the second upper intermediate portion passes essentially through an axis A3 and the second lower intermediate portion passes essentially through an axis A4, A3 and A4 being intersecting and forming an angle greater than or equal to 45°, in particular greater than or equal to 90°.

In a subvariant of embodiment, the first upper and lower intermediate portions each include a free end.

In some embodiments, the second upper and lower intermediate portions each include a free end.

In particular, the first intermediate zone of the first intermediate arm is an interruption zone of this arm.

In particular, the second intermediate zone of the second intermediate arm is an interruption zone of this arm.

In a subvariant, the first intermediate zone is a bending zone of the first intermediate arm.

In some embodiments, the second intermediate zone is a bending zone of the second intermediate arm.

In a variant of embodiment, the first armature includes at least one portion of an elongated element acting as a leaf spring, in particular the first intermediate arm includes at least one leaf spring.

In some embodiments, the second armature includes at least one portion of an elongated element acting as a leaf spring, in particular the second intermediate arm includes at least one leaf spring.

In a variant of embodiment, at least one of the at least partially metallic elongated elements includes at least one twisted portion in position A or B, and the twisted portion is untwisted when it changes position between positions A and B.

Preferably, the first lateral spring and/or the second lateral spring each include at least one twisted portion.

For example, this arrangement can be obtained by moving the first (or second) lateral spring from position B to position A, the first (or second) spring being in a frontal plane F1 (or F2) in position B and in a sagittal plane S1 (or S2) essentially intersecting to F1 (or F2), in particular essentially perpendicular to F1 (or F2), in position A. The first (or second) lateral spring is then deformed to the point that at least one portion of the elongated element is twisted. When the first (or second) lateral spring moves into position B, the twisted portion is twisted in the opposite direction, and therefore untwisted.

This variant defines a third position A for the first and/or second lateral spring(s).

Preferably, when the at least one twisted portion is formed, the distance separating the first (or second) upper and lower portions is increased or decreased.

In a variant, the first intermediate arm has a thickness e0 in its first intermediate zone which is less than the thickness e1 of the first upper intermediate portion and/or than the thickness e2 of the first lower intermediate portion.

In some embodiments, the second intermediate arm has a thickness e3 in its second intermediate zone which is less than the thickness e4 of the second upper intermediate portion and/or than the thickness e5 of the second lower intermediate portion. The first or second intermediate zone is thus for the first or second intermediate arm a zone of weakness allowing bending the first or second upper and lower intermediate portions towards each other.

In a variant of embodiment, the implantable device includes a second lateral spring including a second armature including one or more at least partially metallic elongated elements.

This is the second lateral spring described in the present text.

In a variant of embodiment, the implantable device includes a main armature including the first armature and the second armature, and the main armature extends partly through the intervertebral wedge.

In one embodiment, the first armature and the second armature are joined together by means of one or more junction arms, in particular the junction arms extend at least partially through the intervertebral wedge, especially between the front and rear zones of the intervertebral wedge or between the first and second lateral zones of the intervertebral wedge. The junction arms preferably include at least one elongated metallic element according to the disclosure.

In a variant of embodiment, the first lateral spring has an essentially first loop shape.

In some embodiments, the second lateral spring has an essentially second loop shape.

Preferably, the first loop and/or the second loop each include a central empty zone.

The central empty zone facilitates moving from position B to position A, and vice versa, since there is no obstacle to bringing together or separating the (first or second) upper and lower portions from each other of the first and/or second lateral spring(s). In a variant, the first armature, and, optionally, the second armature, are coated completely or partially with at least one material chosen from: polymers, textiles and a combination of these.

Preferably, the at least partially metallic, especially metallic, elongated elements are coated, in particular overmoulded, with at least one polymer material, more particularly chosen from elastomers, such as silicones and polyurethanes. In a variant, the first lateral spring and/or the second lateral spring include one or more portions which lack the at least partly metallic elongated element, in particular including at least one polymer material, in particular elastomeric.

In a variant, the first lateral spring and/or the second lateral spring include a first and/or a second polymeric intermediate arm, in particular lacking an elongated metal element. Preferably, the first intermediate polymeric arm is in connection with the first upper and lower arms of the first armature, and/or the second intermediate polymeric arm is in connection with the second upper and lower arms of the second armature.

In a variant, the first upper arm and/or the first lower arm and/or the first intermediate arm and/or the first upper intermediate portion and/or the first lower intermediate portion and/or the second upper arm and/or the second lower arm and/or the second intermediate arm, and/or the second upper intermediate portion and/or the second lower intermediate portion and/or the junction arm or arms, each include at least one at least partly metallic elongated element optionally coated with at least one polymer material.

In a variant, the first lateral spring includes a cranial part and a caudal part, and the cranial part is inclined with respect to the caudal part, in particular by an angle $\alpha 1$.

Preferably, the angle $\alpha 1$ is less than or equal to 60°, preferably less than or equal to 50°, more preferably less than or equal to 40°, preferentially greater than or equal to 15°. This arrangement of the first lateral spring allows ensuring that the implantable device has good anatomic conformability in the interlaminar space and in the neighboring interspinous space. The implantable device is thus more stable in its implantation position.

Indeed, when the implantable device is in its implantation position, the cranial part of the first lateral spring abuts against the lower lamina of the overlying or upper vertebra while the caudal part of the first lateral spring abuts against the upper lamina of the underlying or lower vertebra.

The first lateral spring forms a retention component configured to come into abutment against the lamina of the overlying and underlying vertebrae and prevent any anterior migration, i.e., towards the dural space, of the intervertebral wedge and therefore of the device.

The inclination of the cranial part, in particular the posterior inclination of the cranial part, relative to the caudal part advantageously makes it possible to ensure optimised contact because it adapts to the natural inclination formed between the upper lamina and the lower lamina of the overlying and underlying vertebrae treated.

The implantable device is thus more stable in its implantation position and improves its functions of support and maintenance of intervertebral spacing.

In the present text, cranial part is understood to mean any part oriented towards the head of the subject treated when the implantable device is in its implantation position.

In the present text, caudal part is understood to mean any part far from the head and therefore oriented towards the feet of the subject treated when the implantable device is in its implantation position.

Posterior inclination is understood to mean that the part, in the implantation position, is inclined towards the rear or the posterior side of the subject treated in the standing position.

Preferably, the angle $\alpha 1$ and/or the angle $\alpha 2$ (below) and/or the angle $\beta 1$ are measured in the counterclockwise direction.

In one embodiment, the cranial part of the first lateral spring has its greatest height Hcr, in particular the height of its anterior face, lower than the greatest height Hca of the caudal part of the first lateral spring, in particular the height of the anterior face of the caudal part.

The greater height is understood to mean that the part can have different heights but that the height considered is the greatest measured.

In one embodiment, a junction between the cranial part and the caudal part is at a distance dcr from a plane (Tap1) passing through the upper bearing zone and at a distance dca from a plane (Tap2) passing through the lower bearing zone, dcr being less than dca.

In a variant of embodiment, the first lateral spring includes a first armature including first upper and lower arms and the first upper arm is inclined with respect to the first lower arm, in particular at the angle $\alpha 1$.

In a variant of embodiment, the cranial part of the first lateral spring includes the first upper arm and, optionally, the first upper intermediate portion of a first intermediate arm.

In one embodiment, the caudal part of the first lateral spring includes the first lower arm, and, optionally, the first lower intermediate portion of a first intermediate arm.

In a variant, the second lateral spring includes a cranial part and a caudal part, and the cranial part is inclined relative to the caudal part, in particular by an angle $\alpha 2$.

Preferably, the angle $\alpha 2$ is less than or equal to 60°, preferably less than or equal to 50°, more preferably less than or equal to 40°, preferentially greater than or equal to 15°.

This arrangement of the second lateral spring allows ensuring that the implantable device has good anatomical conformability in the interlaminar space and in the neighboring interspinous space. The implantable device is thus more stable in its implantation position.

In one embodiment, the second lateral spring includes a second armature including second upper and lower arms, and the second upper arm is inclined with respect to the second lower arm, in particular by the angle $\alpha 2$.

In one embodiment, the cranial part includes the second upper arm and, optionally, the second upper intermediate portion of a second intermediate arm.

In one embodiment, the caudal part includes the second lower arm and, optionally, the second lower intermediate portion of a second intermediate arm.

The first upper and lower arms and/or the second lower and/or upper arms may comprise/have any of the characteristics defined in the present text.

In a variant, the caudal and cranial parts of the first lateral spring include a first armature at least partially coated, preferably completely coated, with a polymeric material, optionally in combination with a textile material.

In a variant, the caudal and cranial parts of the second lateral spring include a second armature, at least partially coated, preferably completely coated, with a polymeric material, optionally in combination with a textile material.

In a variant, the cranial part includes an anterior face including a region passing through a plane Pa and the caudal part includes an anterior face including a region passing through a plane Pb, the planes Pa and Pb being intersecting, in particular forming the angle $\alpha 1$ (for the first lateral spring) or the angle $\alpha 2$ (for the second lateral spring).

The cranial part and the caudal part can be those of the first armature or of the second armature.

Preferably, the angle is measured in the counterclockwise direction.

The anterior surface of the cranial part can be included in the plane Pa.

The anterior face of the caudal part can be included in the plane Pb.

The plane Pb is preferably essentially parallel to the frontal plane F.

In a variant, the intervertebral wedge includes an anterior face including at least one region passing essentially through a plane Pc, the planes Pb and Pc being intersecting.

The anterior surface of the intervertebral wedge can be included in the plane Pc.

Preferably, the planes Pc and Pb form an angle $\beta 1$ greater than 0° and less than or equal to 30°, in particular less than or equal to 20°.

The intervertebral wedge includes an anterior face inclined relative to the plane Pb passing through the region of the anterior face of the caudal part of the first lateral spring.

In a variant, the anterior face of the intervertebral wedge passes through a plane Pc forming an angle $\Theta$ with a plane Tap1 passing through the upper bearing zone of the wedge or a plane Tap2 passing through the lower bearing zone of the wedge, the angle $\Theta$ is greater than or equal to 30° and less than or equal to 90°, in particular greater than or equal to 50°, especially greater than or equal to 60°. In a variant, the intervertebral wedge includes at least one elastomeric polymer material, in particular chosen from silicones or polyurethanes.

In a variant of embodiment, the intervertebral wedge includes an outer textile envelope, in particular at least partially enveloping a core in at least one polymer material.

The core is preferably made of at least one elastomeric polymer material, especially chosen from silicones and polyurethanes.

According to a second aspect, the present disclosure relates to an ancillary for handling an implantable device according to any one of the variants of embodiment with reference to the first aspect of the disclosure. The ancillary includes a gripping device and a device configured to allow the implantable device in its insertion position to be put into a hollow elongated element and to allow the implantable device to leave the hollow elongated element.

The ancillary can also be configured to help deploy the implantable device when it moves from its insertion position to its implantation position.

The hollow elongated element is preferably a trocar.

DESCRIPTION OF THE DRAWINGS

The disclosure will be better understood upon reading the description which follows of embodiments of the disclosure, given by way of non-limiting examples, in reference to the attached drawings, in which:

FIG. 1 schematically illustrates, in perspective view, and along its front face, a first example of an implantable device according to the disclosure in the implantation position, the first and second lateral springs being in position B;

FIG. 2 schematically illustrates, in perspective view, and along its rear face, the implantable device shown in FIG. 1;

FIG. 3 schematically illustrates, in top view, the implantable device shown in FIGS. 1 and 2;

FIG. 4 schematically shows, in perspective view, the main armature of the implantable device shown in FIGS. 1 to 3;

FIG. 5 schematically shows, in perspective and viewed along its front face, the implantable device shown in FIGS. 1 to 3 in an insertion position in which the first and second lateral springs are in a first position A;

FIG. 6 schematically shows, in perspective and viewed along its front face, the implantable device shown in FIGS. 1 to 3 in an insertion position in which the first and second lateral springs are in a second position A;

FIG. 7 schematically shows, in perspective and viewed along its front face, the implantable device shown in FIGS. 1 to 3 in an insertion position in which the first and second lateral springs are in a third position A;

FIG. 8 schematically illustrates, in perspective view, and along its front face, a second example of an implantable device according to the disclosure in the implantation position;

FIG. 9 schematically illustrates, in perspective and exploded view and along its rear face, the second example of an implantable device shown in FIG. 8 in the implantation position;

FIG. 10 schematically illustrates, in perspective view, along its front face, a third example of an implantable device according to the disclosure in the implantation position;

FIG. 11 schematically illustrates, in perspective view and along its front face, a fourth example of an implantable device according to the disclosure in the implantation position;

FIG. 12 schematically illustrates, in perspective view and along its front face, a fifth example of an implantable device according to the disclosure;

FIG. 13 schematically illustrates, in perspective view and along its front face, a sixth example of an implantable device according to the disclosure;

FIG. 14 schematically illustrates, in perspective view and along its rear face, the sixth example of implantable device shown in FIG. 13;

FIG. 15 schematically illustrates, in perspective, a seventh example of an implantable device according to the disclosure positioned on a vertebral level to be treated;

FIG. 16 schematically illustrates, essentially along its front face, an eighth example of an implantable device;

FIG. 17 schematically illustrates, in side view, the implantable device shown in FIG. 16 in a position corresponding to its implantation position;

FIG. 18 schematically illustrates, in side view and along a sagittal section plane, the implantable device shown in FIGS. 16 and 17 positioned on a vertebral level to be treated without the posterior articulations; and FIG. 19 schematically illustrates, in side view, the implantable device according to the disclosure positioned on a vertebral level to be treated.

DESCRIPTION OF EMBODIMENTS

The first example of an implantable device 100 shown in FIGS. 1 to 7, especially for maintaining an intervertebral space between overlying and underlying vertebrae, includes an intervertebral wedge 10 including an upper bearing zone 12, in particular on the lamina of the overlying vertebra, and a lower bearing zone 14, in particular on the lamina of the underlying vertebra, separated by a minimum distance Da for maintaining an intervertebral space. The device 100 includes a first lateral spring 20 having a height H1 in a position A corresponding to the insertion position of the device 100 and a height H2 in a position B corresponding to an implantation position of the device 100, H2 being different from H1. The device 100 also includes a second lateral spring 40 having a height H11 in a position A corresponding to an insertion position of the device 100 and a height H22 in a position B, corresponding to an implantation position of the device 100, H22 being different from H11. The first lateral spring 20 and the second lateral spring 40 are each configured to freely translate from position A to position B under the effect of their intrinsic elasticities and each form a retention component arranged relative to the intervertebral wedge 10 to block the migration of the intervertebral wedge 10 towards the spinal canal in position B.

The first lateral spring 20 includes first upper 22 and lower 24 portions separated by D1 in position A, and separated by D2 in position B, D2 being different from D1. The second lateral spring 40 includes first upper 42 and lower 44 portions separated by D11 in position A, and separated by D22 in position B, D22 being different from D11.

The intervertebral wedge 10 has a maximum height Ha less than H2 and H22 in the implantation position of the device 100.

The first and second lateral springs 20, 40 extend on either side of the sagittal section plane S of the intervertebral wedge 10.

The first upper 22 and lower 24 portions of the first lateral spring 20 project on either side of a transverse section plane T of the intervertebral wedge. Moreover, the second upper 42 and lower 44 portions of the second lateral spring 40 project on either side of a transverse section plane T of the intervertebral wedge 10.

The intervertebral wedge 10 includes the first and second lateral zones 5, 6, especially positioned on either side of the sagittal section plane S of the intervertebral wedge 10. The intervertebral wedge 10 also includes the front and rear zones 7, 8 positioned on either side of the frontal section plane F of the intervertebral wedge 10.

The first lateral spring 20 includes a first armature 50 and the second lateral spring 40 includes a second armature 60.

The first and second armatures 50, 60 form a main armature 70, shown alone in FIG. 4, crossing through the intervertebral wedge 10, from its first lateral zone 5 to its second lateral zone 6. In this specific example, the main armature 70 includes a single elongated element 65, especially metallic, such as a ribbon. The elongated element 65 is preferably made of Nitinol. The composition of the alloy is, for example, determined so that if the As temperature is around 17° C., thus at room temperature, for example around 20° C., the main armature 70 is in a superelastic state.

The first armature 50 includes the first upper arm 51 and lower arm 53 extending from the first lateral zone 5 diverging from one another, as well as a first intermediate arm 55 in connection at its ends with the first upper arm 51 and lower arm 53. The first intermediate arm 55 includes the first upper intermediate portion 56 and lower intermediate portion 57 converging towards a first intermediate zone 58, a bending zone in this specific example, and around which the first upper intermediate portion 56 and lower intermediate portion 57 pivot, in particular around the axis P1, when moving from position A to position B, and vice versa.

The first upper arm 51 passes through an axis L1 and the first lower arm 53 passes through an axis L2; L1 and L2 define between them an angle α greater than 90° in position B shown especially in FIG. 4.

The second upper arm 66 passes through an axis L3 and the second lower arm 63 passes through an axis L4; L3 and L4 define between them an angle greater than 90°.

The second armature 60 includes the second upper arm 61 and lower arm 63 extending from the second lateral zone 6 diverging from one another, as well as a second intermediate arm 65 in connection at its ends with the second upper arm 61 and lower arm 63. The second intermediate arm 65 includes second upper intermediate portion 66 and lower intermediate portion 67 converging towards a second intermediate zone 68, in particular a bending zone, and around which the second upper intermediate portion 66 and lower intermediate portion 67 pivot, in particular around the axis P2, when moving from position A to position B.

The first and second armatures 50 and 60 are each in the form of a loop, such as wings, in particular including a central empty space facilitating the deformations of the first and second springs 20 and 40.

The first and second intermediate zones 58, 68 are, in this specific example, bending zones 59, 69 essentially centered, respectively, on the first and second intermediate arms 55, 65. The bending zone 59 has a thickness e0 less than the thickness e1 of the first upper intermediate portion 56 and the thickness e2 of the first lower intermediate portion 57. The bending zone 69 has a thickness e3 less than the thickness e4 of the second upper intermediate portion 66 and the thickness e5 of the second lower intermediate portion 67.

In this specific example, and optionally in combination with different variants of the disclosure, the first and second intermediate arms 55, 65 are also leaf springs.

In operation, the implantable device 100 is positioned in its insertion position, by exerting a mechanical constraint that makes it possible to move the first and second upper portions 22, 42 and lower portions 24, 44 closer together or further apart.

In a first position A shown in FIG. 5, the implantable device 100 can be positioned in a tube 80 according to the arrow f1, for example a trocar, the inner diameter of which is less than H2 and H22, so that the first and second lateral springs 20 and 40, respectively, have reduced heights H1' and H11' compared to heights H2 and H22. Likewise, the distances separating the first and second upper and lower portions (22, 24; 42, 44) are reduced, respectively, along the distances D1' and D11'. In this case, the intervertebral wedge 10 is first inserted along its first or second lateral face 5 or 6.

In a second position A shown in FIG. 6, the first and second lateral springs 20 and 40 are folded against the lateral zones 5 and 6, respectively, of the intervertebral wedge 10. The first and second lateral springs 20 and 40, positioned respectively in frontal planes F1 and F2 (not shown) in position B, essentially parallel to the frontal plane F, are deformed to be positioned respectively in sagittal planes S1 and S2 (not shown) in the second position A, the planes S1 and S2 being essentially parallel to the sagittal plane S. The implantable device 100 can then be inserted into the trocar 80 in the direction of the arrow f2. In this case, the intervertebral wedge 10 is first inserted by its front face 7 or its rear face 8 into the trocar 80. The first and second upper and lower portions of each of the first and second lateral springs 20, 40 are brought together, leading to a reduction in the heights H2 and H22 to H1" (not shown) and H11", and therefore a reduction in the distances D2 and D22 to D1" (not shown) and D11". In this position A, the first and second springs 20 and 40 each include a portion of a twisted elongated element 65, respectively 27 and 47.

In a third position A shown in FIG. 7, the implantable device 100 is positioned in a tube 80 according to the direction of insertion corresponding to the arrow f3. The tube 80 is, in this specific example, a trocar whose inner diameter is determined so that it is less than the footprint of the implantable device 100 in the implantation position and considered according to the direction of insertion f3. In this case, the intervertebral wedge 10 is first inserted into the trocar via its lower face 14 or upper face 12. The first and second upper and lower portions (22, 24; 42, 44) of the springs (20, 40) are moved apart so that the first and second lateral springs 20 and 40, respectively, have increased heights H1''' and H11" with respect to heights H2 and H22. Likewise, the distances separating the first and second upper and lower portions (22, 24; 42, 44) are increased to distances D1''' and D11".

For the first three positions A represented schematically in FIGS. 5 to 7, the footprint of the device 100 being reduced in at least one direction f1, f2 or f3, the device is routed to the vertebral level to be treated by being brought from the proximal end to the distal end of the trocar 80. Once released on the operating site, the implantable device 100 is positioned in the implantation position, under the effect of the body temperature activating the memory of the trained form of the main armature 70 corresponding to position B, and/or under the effect of leaf springs of the first and second intermediate arms 55, 65 accompanying this deployment. The first and second lateral springs 20, 40 thus freely translate from the first/second/third position A to position B, i.e., due to their intrinsic elasticities and not by means of clamping and/or deformation holding the springs 20, 40 in position B.

The second implantable device 200 shown in FIGS. 8 and 9 in its implantation position differs from the device 100 in that its main armature 210 is joined to the rear face 220 of the intervertebral wedge 230 via the protrusions 232, 234. The intervertebral wedge 230 is thus overmoulded over the main armature 210. During overmoulding, the protrusions 232 and 234 for joining the intervertebral wedge 230 to the armature 210 are formed. Preferably, the moulded intervertebral wedge 220 includes at least one elastomeric polymer material, in particular chosen from silicones and polyurethanes.

The main armature 210 includes first and second lateral springs 212 and 214 in an elongated metal element, in particular with shape memory (e.g., Nitinol). These first and second springs 212, 214 include zones of reduced thickness or bending zones, thus forming leaf springs. The main armature 210 includes first and second intermediate arms 250 and 260 each including a zone of reduced thickness or bending zone 251 and 261, respectively.

The main armature 210 also includes first upper arm 270 and lower arm 275 including the reduced thickness or bending zones 271 and 276. Likewise, the main armature 210 includes second upper arm 280 and lower arm 285, each including a reduced thickness or bending zone 281 and 286, respectively.

These bending zones 251, 261, 271, 276, 281, 286 facilitate the deformation of the first and second springs 212, 214 for the moving their first and second upper and lower portions closer together or further apart, and the elastic return of the armature 210 when the mechanical constraint is no longer applied. Except for the additional bending zones defined above, main armature 210 is similar to armature 70. The first upper and lower arms 270, 275 and the first intermediate arm 250 form a first armature 255. The second upper arm 280 and lower arm 285 and the second intermediate arm 260 form a second armature 265. The first and second armatures 255, 265 are joined together at a junction arm 215. The first and second lateral springs 212 and 214, especially their respective armatures 255 and 265, are each in the form of a loop, such as wings, in particular including a central empty space facilitating the deformations of the first and second springs 212 and 214. In this specific case, the main armature 210 is formed from a single elongated metal element, so that the junction arm 215 includes the superposed free ends of the elongated element folded back on itself. The ends of the elongated element can be held together by gluing, welding and/or by the protrusions 232 and 234 or even by an overmoulded part of the intervertebral wedge 230.

The third example of implantable device 300 shown in FIG. 10 includes an intervertebral wedge 330 and a main armature 310 including a first lateral spring 312 and a second lateral spring 314 represented in position B. In this specific example, the main armature 310 includes two distinct elongated metal elements 313 and 315, for example made of Nitinol, respectively forming the first lateral spring 312 and the second lateral spring 314. In particular, the elongated elements 313 and 315 are each in the form of a loop. The intervertebral wedge 330 is preferably overmoulded over the elongated elements 313 and 315. The first lateral spring 312 includes a first armature formed from the elongated element 313 and the second lateral spring 314 includes a second armature formed from the elongated element 315. The operation of the implantable device 300 is similar to that of the implantable devices 100 or 200.

The implantable device 400 shown in FIG. 11 includes an intervertebral wedge 430 as well as a first armature 410 and a second armature 420 respectively including the elongated elements (470, 480). The first armature 410 includes the first upper arm 411 and lower arm 412 as well as a first intermediate arm 413 connected at its ends with the first upper arm 411 and lower arm 412. The second armature 420 has a construction similar to the first armature 410. The first and second armatures 410 and 420 form a main armature of the implantable device 400 but are independent of each other. The first upper arm 411 and lower arm 412 are connected via a junction arm 414 passing through the intervertebral wedge 430, in particular from the upper bearing zone 431 toward the lower bearing zone 432. In this specific example, the first and second armatures 410 and 420 are overmoulded with a polymer coating 440, in particular an elastomer coating. This polymer coating conforms to the armatures 410 and 420. The first and second armatures 410, 420 can be overmoulded in a first step to form the polymer coating, then the intervertebral wedge 430 can be overmoulded in a second step around certain parts of the first and second lateral springs (450, 460) in order to join them to the intervertebral wedge 430. The intervertebral wedge 430 and polymer coating 440 can alternatively be moulded at the same time in a single step. The polymer coating 440 protects the surrounding tissues of the area where the metal armatures 410, 420 are implanted. The first spring 450 thus includes the first armature 410 coated with at least one polymer and the second spring 460 includes the second armature 420 coated with at least one polymer. In this specific example, the first and second springs 450 and 460 are in the form of a loop. The first intermediate arm 413 can include an intermediate zone 416 which is either a bending zone as shown in FIG. 11 (especially with a reduced thickness of elongated element 470) making it easier to bring the first upper and lower portions together, on the one hand, or an interruption zone of the armature 410 in which the free ends of the first upper and lower portions emerge (not shown). The second intermediate arm 423 can be arranged in the same way as the first intermediate arm 416 by means of the intermediate zone 426.

The implantable device 500 shown in FIG. 12 includes, in its implantation position, a first lateral spring 540 and a second lateral spring 560. The first lateral spring 540 includes a first armature 510 including first upper 511 and lower 512 arms connected at their ends with a first intermediate arm 513. The first intermediate arm 513 includes the first upper intermediate portion 514 and lower intermediate portion 515 converging towards an intermediate zone 516 around which the first upper intermediate portion 514 and lower intermediate portion 515 pivot when moving from the insertion position to the implantation position, in particular around the axis P3. The first upper 514 and lower 515 intermediate portions each include a free end 517 and 518. The second lateral spring 560 includes a second armature 520 similar to the first armature 510. The first and second armatures 510, 520 form a main armature including two distinct elongated metal elements, for example in elastic stainless steel or Nitinol. The first armature 510 is in connection with the second armature 520 according to two junction arms 522, 524 crossing through the intervertebral wedge 530 from its first lateral zone toward its second lateral zone. In this specific example, the first and second armatures 510, 520 are coated with a coating 525 including at least one polymer material. This coating can be replaced by a textile material or a combination of at least one textile material with at least one polymer material (in the form of a coating or an impregnation or a film or at least one polymer overmoulded on the textile material). The first and second lateral springs 540 and 560 each have the general shape of a loop with an empty internal region 505. The coating 525 in at least one polymer material also coats the intermediate zone 516 and forms the junction between the free ends 517, 518 so that the first intermediate arm 513, although discontinuous, is coated with a continuous coating. Preferably, the polymer material is elastomeric, i.e., it has a high elasticity that does not impede the pivoting of the first upper intermediate portions 514 and 515 toward each other. The implantable device 500 may also not include a first intermediate arm 513 or a second intermediate arm 523. In this case, the first and second lateral springs 540 and 560 are still in the form of a loop but include first and second polymeric intermediate arms with no armature and therefore no elongated metallic element.

The implantable device 600, shown in FIGS. 13 and 14, in its implantation position, includes an intervertebral wedge 630 and first and second lateral springs 610 and 620 each respectively including a first armature 640 and a second armature 660. The first armature 640 includes the first upper arm 641 and lower arm 642. The second armature 660 includes the second upper arm 661 and lower arm 662. The first armature 640 is connected to the second armature 660 by means of two upper and lower junction arms 622 and 624 projecting from the rear zone 632 of the intervertebral wedge 630, each essentially forming an arc of a circle. The main armature of the device 600 thus includes the first and second armatures 610 and 620 as well as the upper junction arm 622 and lower junction arm 624. The first and second lateral springs 610 and 620 each have essentially the general shape of a loop, such as wings. The first lateral spring 610 includes a first polymeric intermediate arm 613 not including any elongated metal element. Likewise, the second lateral spring 620 includes a second polymeric intermediate arm 623 not including any elongated metal element. Preferably, the main armature is coated, in particular by overmoulding, with at least one elastomeric polymer material. During overmoulding, the first and second polymeric intermediate arms 613 and 623 are moulded. These arms 613 and 623 contribute to the stabilisation and deployment of the first and second lateral springs 610 and 620. The polymeric intermediate arms 613 and 623 are less rigid than metal intermediate arms (such as those of the first and second armatures according to the disclosure), thus making it possible to very perceptibly reduce the stiffness constant of the first and second springs. Moving from the implantation position to the insertion position for inserting the implantable device into the trocar(s) is relatively easier. In addition, in the implantation position, if a contact occurs between the upper and lower portions of the first or second lateral spring, on the one hand and, on the other hand, the bony parts of the surrounding spine following an extension movement of the spine, the first or second spring deforms easily and does not block the movements of the spine. The implantable device 700 shown in FIG. 15 in its implantation position includes an intervertebral wedge 730 and first and second lateral springs 710 and 720. The intervertebral wedge 730 includes an upper bearing zone 731 on a portion of the lamina of the overlying vertebra 780 and a lower bearing zone 732 on a portion of the lamina of the underlying vertebra 790. The intervertebral wedge 730 makes it possible to maintain a minimum intervertebral spacing of at least Da corresponding to the distance separating the upper bearing zone 731 from the lower bearing zone 732. The first and second lateral springs 710 and 720 have heights in the implantation position H2 and H22, respectively, greater than Da and, in particular, project on either side of the upper and lower bearing zones 731 and 732. This particular arrangement allows the first and second lateral springs 710 and 720 to also act as retention components preventing the migration of the intervertebral wedge 730 towards the spinal canal.

Preferably, and as can be seen in the figures, the first and second lateral springs of the implantable devices 100 to 600 are arranged similarly in the implantation position to the lateral springs 710 and 720 in order to act as retention components preventing migration of the intervertebral wedge to the spinal canal.

The implantable device 800 shown in FIGS. 16 to 19 in an implantation position B includes an intervertebral wedge 810 including an upper bearing zone 812 and a lower bearing zone 814 separated by Da. The device 800 includes a first lateral spring 820 and a second lateral spring 840 each forming a retention component to block the migration of the wedge forward in the implanted position. The first and second lateral springs have heights H1 and H2, respectively. The first and second lateral springs 820, 840 include cranial part 830, 850 and caudal part 860, 870. The cranial part 830 is inclined relative to the caudal part 860, in particular posteriorly, so as to form an angle $\alpha 1$ (not shown) of less than 60°, for example of around 20°. Likewise, the cranial part 850 is inclined relative to the caudal part 870, in particular posteriorly, so as to form an angle $\alpha 2$ of less than 60°, for example of around 20° as shown in FIG. 17. The second lateral spring 840 includes a second armature 842 including a second upper arm 844, a second lower arm 846 and a second intermediate arm 848. The second intermediate arm 848 includes a second upper intermediate arm portion **848*a* and a second lower intermediate arm portion 848*b*. The cranial part 850 thus includes the second upper arm 844 and the second upper portion of the intermediate arm 848*a*. The caudal part 870 includes the second lower arm 846 and the second lower portion of intermediate arm 848*b*. The cranial 830 part and caudal part 860 are arranged in a similar manner with respect to the first armature of the first lateral spring 820. The front face 807 of the wedge 810 passes through the plane Pc. As can be seen in FIG. 17, the front face 855 of the cranial part 850 passes through the plane Pa and the front face 875 of the caudal part 870 passes through the plane Pb, the planes Pa and Pb are intersecting and form the angle $\alpha 2$. The same reasoning applies for the caudal part 860 and cranial part 830 of the first lateral spring 820**.

The planes Pb and Pc are also intersecting and form an angle $\beta 1$ less than or equal to 50°, in particular less than or equal to 40°, for example around 5-6°.

The anterior face 855 of the intervertebral wedge 810 passes through the plane Pc forming an angle $\Theta$ with a plane Tap1 passing through the upper bearing zone 812 of the wedge or a plane Tap2 passing through the lower bearing zone 814 of the wedge, the angle $\Theta$ is greater than or equal to 60°.

Finally, the junction 880 between the cranial part 850 and the caudal part 870 is separated by dcr from the plane Tap1 passing through the upper bearing zone 812 and separated by dca from the bearing plane Tap2 passing through the lower bearing zone 814, with dcr being less than dca. It is thus found that the greatest height Hca of the caudal part 870, in particular the height of the anterior face 855, is greater than the greatest height Hcr, in particular the height of the anterior face 875, of the cranial part 850. The inclination of an angle $\alpha 2$ is found between the second lower portion **848*b* and the second upper portion 848*a* as well as between the second upper arm 844 and the second lower arm 846. This inclination of the springs 820 and 840 allows the device to conform to the areas of the spine to be supported, thus improving the support as well as the stability. As shown in FIG. 18, the upper and lower bearing zones 812, 814 rest against the overlying 880 and underlying 885 laminas. The cranial parts 830, 850 abut the lamina of the overlying vertebra 890 and the caudal parts abut the lamina of the underlying vertebra 895 as shown in FIGS. 18 and 19. The combination of the abutment and the anatomical shape of the first and second lateral springs 820, 840** improves the stability and the maintenance of a durable intervertebral space.

The implantable devices 200, 300, 400, 500, 600, 700 and 800 can indifferently adopt one of the first three positions A illustrated in FIGS. 5 to 7 for inserting these devices into a trocar.

The intervertebral wedges of the implantable devices 100 to 800 can be at least partially coated with a textile envelope, in particular the upper bearing zone and/or the lower bearing zone and/or the front zone and/or the rear zone and/or the first lateral zone and/or the second lateral zone may be at least partially coated with a textile envelope. This arrangement has the advantage of initiating colonisation of the surrounding tissues via the porosity of the textile. This colonisation propagates on the surface of the textile and in the thickness of the textile. An additional mechanical attachment between the implantable device and the surrounding tissues is thereby created, which makes it possible to limit the migration of the implantable device toward the spinal canal.

The intervertebral wedges of the devices 100 to 800 are preferably manufactured by overmoulding the main armatures and are preferably made from an elastomer chosen from silicones and polyurethanes.

It is understood that the dimensions of the implantable device according to the disclosure (such as the heights H1', H1", H1", H2, H22, Da, Ha) as well as those of the trocar, are determined according to the specific application, and the desired deformation of the first and second lateral springs.

The invention claimed is:

1. An implantable device for maintaining an intervertebral space between overlying and underlying vertebrae, the implantable device comprising:

an intervertebral wedge comprising an upper bearing zone configured to bear against at least a portion of the lamina of the overlying vertebra, and a lower bearing zone configured to bear against at least a portion of the lamina of the underlying vertebra, said upper bearing zone and said lower bearing zone being separated by a minimum distance Da to maintain an intervertebral space, wherein the intervertebral wedge is configured to be received in an interlaminar space between said laminae, and the intervertebral wedge includes further first and second lateral faces extending between said upper and lower bearing zones, and front and rear faces extending between said upper and lower bearing zones, and said implantable device further comprises:

a first lateral spring and a second lateral spring, each of said first and second lateral springs having a position A relative to the intervertebral wedge in a position for inserting the implantable device and a position B relative to the intervertebral wedge in a position for implanting the implantable device, the positions A and B being different, and wherein both of said first lateral spring and second lateral spring are configured:

to freely translate from position A to position B, and to form a retention component arranged relative to the intervertebral wedge to block the migration of the intervertebral wedge toward the spinal canal in position B, and wherein the first and second lateral springs extend from said first and second lateral faces of the intervertebral wedge respectively, wherein said implantable device comprises a main armature comprising a first armature and a second armature, and wherein the main armature extends partly through the intervertebral wedge, the first armature and the second armature are joined together by one or more junction arms extending through the intervertebral wedge between said first and second lateral faces of the intervertebral wedge, said junction arm(s) including at least one elongated metallic element, wherein the first lateral spring comprises the first armature comprising one or more at least partially metallic elongated elements, wherein the second lateral spring comprises the second armature comprising one or more at least partially metallic elongated elements, wherein the first armature comprises a first upper arm and a first lower arm which diverge from each other, wherein the first armature comprises a first intermediate arm, continuous or discontinuous, in connection with the first upper arm and with the first lower arm, wherein in position A, the first lateral spring and the second lateral spring are folded down respectively against the first and second lateral faces of the intervertebral wedge in order that the first lateral spring is in a sagittal plane S1 and the second lateral spring is in a sagittal plane S2, wherein in position B, the first lateral spring is in a frontal plane F1 and the second lateral spring is in a frontal plane F2, wherein sagittal planes S1 and S2 are intersecting with the planes F1 and F2 respectively, and wherein the intervertebral wedge includes a core in at least one polymer material that is overmoulded over at least a part of the main armature comprising said one or more junction arms, said core being enveloped at least partially by an outer textile envelope.

2. The implantable device according to claim 1, wherein said at least first lateral spring has a height H1 in position A and a height H2 in position B, H2 being different from H1.

3. The implantable device according to claim 1, wherein the first lateral spring comprises at least one material chosen from shape-memory materials.

4. The implantable device according to claim 1, wherein the first lateral spring comprises first upper and lower portions separated by D1 in position A, and separated by D2 in position B, D2 being different from D1 and the implantable device is positioned in the insertion position by bringing together or separating the first upper and lower portions of the first lateral spring.

5. The implantable device according to claim 1, wherein the first lateral spring extends from one side of a sagittal section plane S of the intervertebral wedge.

6. The implantable device according to claim 1, wherein the first intermediate arm comprises first upper and lower intermediate portions converging towards a first intermediate zone around which said first upper and lower intermediate portions pivot when moving from position A to position B.

7. The implantable device according to claim 6, wherein the first intermediate arm has a thickness e0 in its first intermediate zone which is less than one or more of the thickness e1 of the first upper intermediate portion and the thickness e2 of the first lower intermediate portion.

8. The implantable device according to claim 1, wherein the first upper and lower intermediate portions each comprise a free end.

9. The implantable device according to claim 1, wherein the first intermediate zone is a bending zone of the first intermediate arm.

10. The implantable device according to claim 1, wherein the first armature comprises at least one portion of an elongated element acting as a leaf spring.

11. The implantable device according to claim 1, wherein at least one of said at least partially metallic elongated elements comprises at least one twisted portion in position A or B, wherein said twisted portion is untwisted when it changes position between positions A and B.

12. The implantable device according to claim 1, wherein the first lateral spring essentially has the shape of a first loop.

13. The implantable device according to claim 1, wherein the first armature is completely or partially coated with one or more material chosen from: polymers, textiles, and a combination thereof.

14. The implantable device according to claim 1, wherein the first lateral spring comprises a cranial part and a caudal part, and wherein the cranial part is inclined with respect to the caudal part.

15. The implantable device according to claim 1, wherein the cranial part comprises an anterior face comprising a region passing through a plane Pa and the caudal part comprises an anterior surface comprising a region passing through a plane Pb, the planes Pa and Pb being intersecting.

16. The implantable device according to claim 1, wherein the first armature and the second armature include at least one partially elongated metallic element in common.

17. The implantable device according to claim 1, wherein the one or more at least partially elongated metallic element of the first armature are distinct from the one or more at least partially elongated metallic element of the second armature.

18. The implantable device according to claim 1, wherein the intervertebral wedge is preferably dimensioned to fill the interlaminar space treated to be close to the centre of rotation of the overlying and underlying vertebrae and be positioned in the lamina area.

19. The implantable device according to claim 1, wherein the front face of the intervertebral wedge passes through a plane Pc forming an angle Θ with a plane Tap1 passing through the upper bearing zone of the wedge or a plane Tap2 passing through the lower bearing zone of the wedge, the angle Θ is greater than or equal to 30° and less than to 90°.

* * * * *